US012716078B2

(12) United States Patent
McInerney et al.

(10) Patent No.: US 12,716,078 B2
(45) Date of Patent: Aug. 25, 2026

(54) **METHODS OF USING *SYNTROPHUS ACIDITROPHICUS* TO PRODUCE CYCLOHEXANE-1-CARBOXYLATE (CHC)**

(71) Applicant: The Board of Regents of the University of Oklahoma, Norman, OK (US)

(72) Inventors: Michael J. McInerney, Norman, OK (US); Neil Q. Wofford, Norman, OK (US); Ebony Boling, Mustang, OK (US); Elizabeth A. Karr, Norman, OK (US)

(73) Assignee: The Board of Regents of the University of Oklahoma Norman, Norman, OK (US)

( * ) Notice: Subject to any disclaimer, the term of this patent is extended or adjusted under 35 U.S.C. 154(b) by 0 days.

(21) Appl. No.: 18/998,009

(22) PCT Filed: Jun. 11, 2024

(86) PCT No.: PCT/US2024/033400

§ 371 (c)(1),
(2) Date: Jan. 23, 2025

(87) PCT Pub. No.: WO2024/258846

PCT Pub. Date: Dec. 19, 2024

(65) Prior Publication Data

US 2025/0263757 A1 Aug. 21, 2025

Related U.S. Application Data

(60) Provisional application No. 63/508,396, filed on Jun. 15, 2023.

(51) Int. Cl.

| | |
|---|---|
| ***C12P 7/40*** | (2006.01) |
| ***C12N 1/205*** | (2026.01) |
| *C12R 1/01* | (2006.01) |

(52) U.S. Cl.
CPC ................ *C12P 7/40* (2013.01); *C12N 1/205* (2021.05); *C12R 2001/01* (2021.05)

(58) Field of Classification Search
None
See application file for complete search history.

(56) References Cited

PUBLICATIONS

James, et al.; "Syntrophus Aciditrophicus Uses the Same Enzymes in a Reversible Manner to Degrade and Synthesize Aromatic and Alicyclic Acids," Environmental Microbiology (2019), 21(5):1833-1846.
Agne, et al.; "Enoyl-Coenzyme A Respiration via Formate Cycling in Syntrophic Bacteria," mBio (2022) 13(1):e03740-21.
Elshahed, et al.; "Metabolism of Benzoate, Cyclohex-1-ene Carboxylate, and Cyclohexane Carboxylate by "Syntrophus Aciditrophicus" Strain SB in Syntrophic Association with H2-Using Microorganisms," (2001), Applied and Environmental Microbiology 67(4):1728-1738.
Mouttaki, et al.; "Cyclohexane Carboxylate and Benzoate Formation from Crotonate in Syntrophus Aciditrophicus," Applied and Environmental Microbiology (2007) 73(3):930-938.
Mouttaki, et al.; "Use of Benzoate as an Electron Acceptor by Syntrophuys aciditrophicus Grown in Pure Culture with Crotonate," Environmental Microbiology (2008) 10(12):3265-3274.
Tanner, Ralph S.; "Cultivation of Bacteria and Fungi," Manual for Environmental Microbiology—American Society for Microbiology (1996) pp. 52-60.
Boll, et al.; "Fermentative Cyclohexane Carboxylate Formation in Syntrophus Aciditrophicus," Journal of Molecular Microbiology and Biotechnology (2016) 26(1):165-179.
Mcinerney, et al.; "Syntrophy in Anaerobic Global Carbon Cycles," Current Opinion in Biotechnology (2009), 20(6):623-632.
Elshahed, et al. "Benzoate Fermentation by the Anaerobic Bacterium Syntrophus Aciditrophicus in the Absence of Hydrogen-Using Microorganisms," Applied and Environmental Microbiology, American Society for Microbiology (2001) 67(12):5520-5525.
International Search Report dated Dec. 5, 2024, in PCT/US2024/033400, filed Jun. 11, 2024.
Written Opinion of the International Searching Authority dated Dec. 5, 2024, in PCT/US2024/033400, filed Jun. 11, 2024.

*Primary Examiner* — Richard G Hutson
(74) *Attorney, Agent, or Firm* — Dunlap Codding, P.C.

(57) ABSTRACT

A method of producing cyclohexane-1-carboxylate (CHC), including providing a growth medium comprising a yeast extract, and a crotonate salt; providing a culture of *Syntrophus aciditrophicus* (*S. aciditrophicus*); using the growth medium to initiate growth of the culture of *S. aciditrophicus*; after the *S. aciditrophicus* has initiated cell division, adding to the growth medium a benzoate salt, wherein after an incubation period, the CHC produced by the culturing of the *S. aciditrophicus* in the growth medium is purified. The incubation period may be continued until the amount of CHC in the growth medium has achieved a concentration of at least 1 g/l (7.8 mM).

24 Claims, 4 Drawing Sheets

METHODS OF USING *SYNTROPHUS ACIDITROPHICUS* TO PRODUCE CYCLOHEXANE-1-CARBOXYLATE (CHC)

CROSS REFERENCE TO RELATED APPLICATIONS/INCORPORATION BY REFERENCE STATEMENT

This application is a US National Stage Application under 35 USC § 371 of International Application No. PCT/US2024/33400, filed Jun. 11, 2024; which claims benefit of U.S. Provisional Application Ser. No. 63/508,396, filed Jun. 15, 2023. The entirety of the above-referenced patent application(s) are hereby expressly incorporated herein by reference.

BACKGROUND

*Syntrophus aciditrophicus* (*S. aciditrophicus*) is a strictly anaerobic microorganism that produces cyclohexane-1-carboxylate (CHC) when grown with crotonate in pure culture. *S. aciditrophicus* also reduces benzoate to CHC in the presence of crotonate, and ferments benzoate to acetate and CHC. The pathway for benzoate, crotonate and CHC metabolism is shown in FIG. 1. Based on proteomic, enzymatic, and metabolomic analyses, it was determined that *S. aciditrophicus* uses the same set of enzymes to metabolize benzoate, CHC, and crotonate to acetate and to synthesize CHC from crotonate and acetate (K. L. James, J. W. Kung, B. R. Crable, H. Mouttaki, J. R. Sieber, H. H. Nguyen, Y. Yang, Y. Xie, J. Erde, N. Q. Wofford, E. A. Karr, J. A. Loo, R. R. Ogorzalek Loo, R. P. Gunsalus, and M. J. McInerney. 2019. *Syntrophus aciditrophicus* uses the same enzymes in a reversible manner to degrade and synthesize aromatic and alicyclic acids. Environ. Microbiol. 21(5): 1833-1846). The pathway is reversible. Agne et al. (2022) showed that formate addition increased the amount of CHC made (Agne, M., L. Appel, C. Seelmann, M. Boll. 2022. Enoyl-coenzyme A respirations via formate cycling in syntrophic bacteria. mBio 13: e03740-21). *S. aciditrophicus* metabolizes some fatty acids and produces trace amounts of glutarate and pimelate as metabolites when grown in the presence of a partner microorganism (M. S. Elshahed, V. K. Bhupathiraju, N. Q. Wofford, M. A. Nanny, and M. J. McInerney. 2001. Metabolism of benzoate, cyclohex-1-ene carboxylate and cyclohexane carboxylate by *Syntrophus aciditrophicus* strain SB in syntrophic association with $H_2$-using microorganisms. Appl. Environ. Microbiol. 67:1728-1738).

*S. aciditrophicus* ferments crotonate according to the following equation 1 (H. Mouttaki, M. A. Nanny, and M. J. McInerney. 2007. Cyclohexane carboxylate and benzoate formation from crotonate in *Syntrophus aciditrophicus*. Appl. Environ. Microbiol. 73: 930-938.0):

$$6\ \text{Crotonate}+CO_2+5\ H_2O\rightarrow 9\ \text{Acetate}+1\ \text{Cyclohexane-1-carboxylate} \quad \text{(Eq. 1)}$$

When benzoate is present, crotonate is oxidized to acetate and benzoate is reduced to cyclohexane-1-carboxylate according to the following equation 2 (H. Mouttaki, M. Nanny, and M. J. McInerney. 2008. Use of benzoate as an electron acceptor by *Syntrophus aciditrophicus* grown in pure culture with crotonate. Environ. Microbiol. 10: 3265-3274.):

$$3\ \text{Crotonate}+1\ \text{Benzoate}+6\ H_2O\rightarrow 6\ \text{Acetate}+1\ \text{Cyclohexane-1-carboxylate} \quad \text{(Eq. 2)}$$

The ratio of crotonate used:CHC produced during *S. aciditrophicus* growth is 6:1 in crotonate fermentation (equation 1). The ratio of crotonate used:benzoate used: CHC produced during *S. aciditrophicus* growth is 3:1:1 for benzoate respiration (equation 2).

Figure 1:
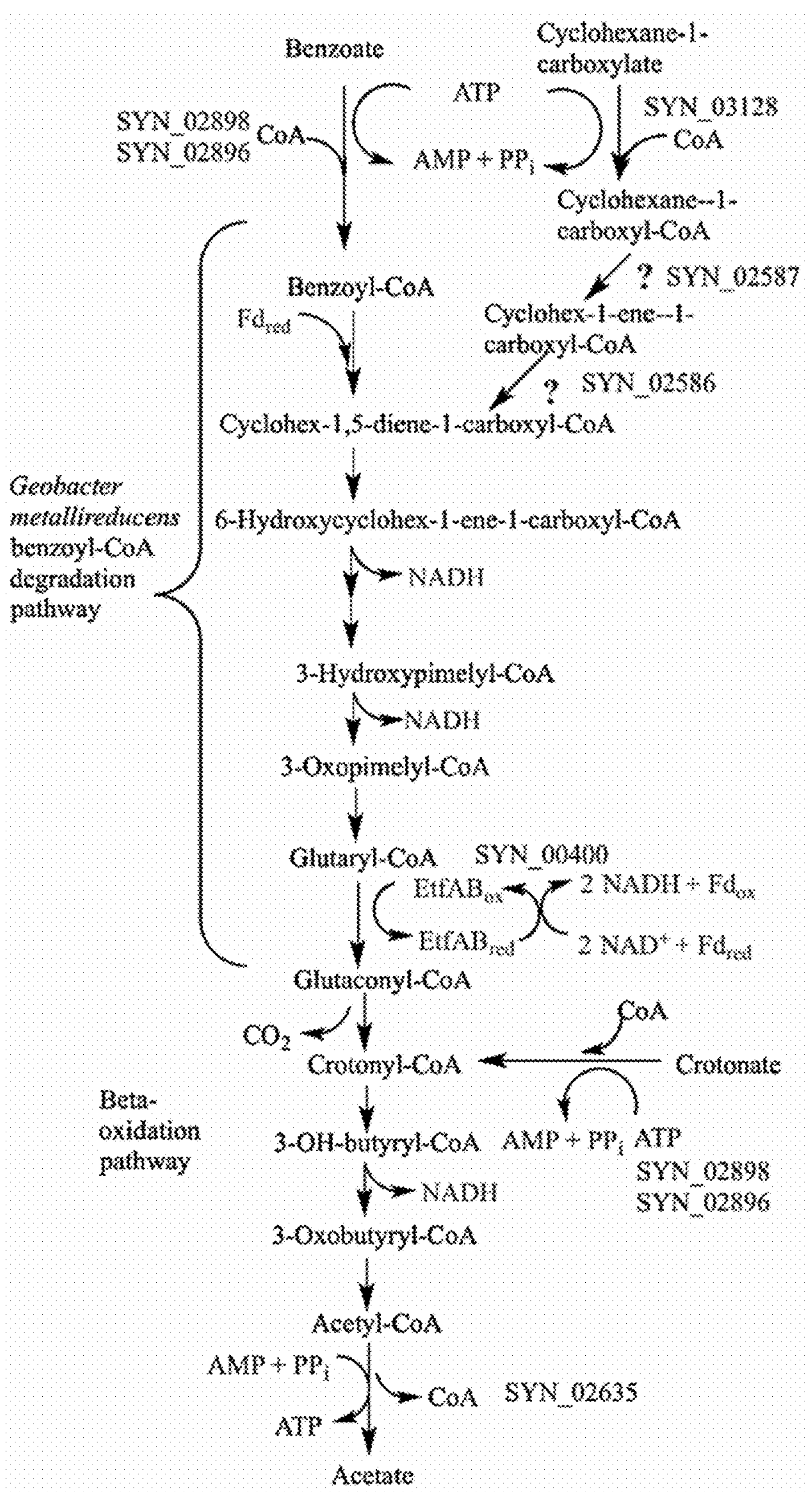
FIG. 1 is a schematic of a pathway for crotonate, benzoate, and CHC metabolism. Gene locus tags are given for some enzymes. Abbreviations: Fd, reduced ferredoxin; EtfAB, electron transfer flavoprotein AB; subscript ox, oxidized; subscript red, reduced.

Abbreviations used herein include:

CA: crotonic acid,

CHC: cyclohexane-1-carboxylate,

1ΔCHC: cyclohex-1-ene-1-carboxylate,

EtfAB, electron transfer flavoprotein AB,

Fd: reduced ferredoxin,

MESA: mercaptoethane sulfonic acid,

Resazurin: 7-hydroxy-3H-phenoxazin-3-one-10-oxide,

RST: R. S. Tanner,

*S. aciditrophicus: Syntrophus aciditrophicus.*

DETAILED DESCRIPTION

The bacterium *S. aciditrophicus* metabolizes the four-carbon organic acid crotonate to make acetate and the 7-carbon molecule cyclohexane-1-carboxylate (CHC). Various nutrient amendments, different crotonate concentrations, additions of formate and benzoate, and different cultural conditions were investigated to determine their effects on the production of CHC. CHC has uses as a base flavor chemical, among other uses.

As described below, it was discovered herein that high crotonate concentrations, particularly of the potassium or sodium salt, the addition of benzoate after bacterial growth had begun, and the addition of a yeast extract increased the amount of CHC to, and above, a level of 1 g/l (7.8 mM). In addition, concentrating the cells after growth and preparing a thick cell suspension with different amounts of crotonate, benzoate, and formate resulted in high CHC concentrations.

The present disclosure, in at least one non-limiting embodiment, is directed to a method of producing CHC, including providing a growth medium comprising a yeast extract, and a crotonate salt; providing a culture of *Syntrophus aciditrophicus* (*S. aciditrophicus*); using the growth medium to initiate growth of the culture of *S. aciditrophicus*; after the *S. aciditrophicus* has initiated cell division, adding to the growth medium a benzoate salt, wherein after an incubation period, the CHC produced by the culturing of the *S. aciditrophicus* in the growth medium is purified. The incubation period may be continued until the amount of CHC in the growth medium has achieved a concentration of at least 1 g/l (7.8 mM).

The present disclosure, in at least one non-limiting embodiment, is directed to a method of producing enhanced amounts (at least 1 g/l) of CHC by growing *S. aciditrophicus* in a growth medium comprising at least 30 mM of a crotonic acid salt, such as but not limited to potassium or sodium crotonate, 5 grams per liter or greater of yeast extract, and about 5 nM to about 20 mM benzoate after bacterial growth has started. In another non-limiting embodiment, the method uses a thick cell suspension of *S. aciditrophicus*, more than 30 mM crotonate (e.g., potassium or sodium crotonate), and more than 10 mM benzoate.

Growing the *S. aciditrophicus* bacterium with high concentrations sodium crotonate (90, 120 and 150 mM) resulted in CHC concentrations of 7 to 13 mM, which was close to or above the target concentration of 7.8 mM CHC. However, production of such high CHC concentrations could not be consistently reproduced with sodium crotonate. Some replicates did not grow well or produced much lower CHC concentrations (low precision). We turned to using potassium crotonate in amounts of 90 and 120 mM, which resulted in CHC amounts of 6.1 to 6.9 mM, which was below the target concentration, but had good consistency (precision) among the replicates. We found that adding yeast extract (Bacto Yeast Extract, Technical Grade, Becton, Dickinson & Co.) to a medium with 20 mM crotonate gave a CHC concentration of 5 mM compared to a CHC concentration of 2.5 mM in the same medium with 20 mM crotonate with no yeast extract. *S. aciditrophicus* respires benzoate with crotonate present. Cultures with 30 mM crotonate, plus 10 mM benzoate provided at the start of growth, made an average of 8.2 mM CHC, which was above the target value. However, it took those cultures more than 30 days to grow and make that level of CHC.

We then tested whether high CHC amounts could be made if we added benzoate after the culture had already started growing. The addition of 5 mM benzoate to already-growing cultures that had 30 mM crotonate made about 5 mM CHC in 12 days, versus over 30 days when benzoate was added at the beginning of incubation. Control cultures where additional crotonate, not benzoate, was added only made 2 mM CHC after 10 days. We then prepared thick cell suspensions of *S. aciditrophicus* and added various concentrations of crotonate, benzoate, and formate. Cell suspensions with 20 to 80 mM crotonate plus 10 mm benzoate plus 5 mM formate made 7.8 to 8.2 mM CHC after only 23 hours. A second cell suspension with 20 to 60 mM crotonate plus 10 to 20 mM benzoate made 6 to 7.7 mM CHC. Cell suspensions with 20 to 60 mM crotonate and no benzoate made only 2.7 to 4.4 mM CHC.

Before further describing various embodiments of the present disclosure in more detail by way of exemplary description, examples, and results, it is to be understood that the compounds, compositions, and methods of present disclosure are not limited in application to the details of specific embodiments and examples as set forth in the description set forth herein. The description provided herein is intended for purposes of illustration only and is not intended to be construed in a limiting sense. As such, the language used herein is intended to be given the broadest possible scope and meaning, and the embodiments and examples are meant to be exemplary, not exhaustive. Also, it is to be understood that the phraseology and terminology employed herein is for the purpose of description only and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure. Thus, while the compounds, compositions, and methods of the present disclosure have been described in terms of particular embodiments, it will be apparent to those of skill in the art that variations may be applied to the compounds, compositions, and methods and in the steps or in the sequence of steps of the methods described herein without departing from the concept, spirit, and scope of the inventive concepts.

All patents, patent applications (including U.S. Provisional Application Ser. No. 63/508,396 filed Jun. 15, 2023), and non-patent publications, including published articles mentioned in the specification or referenced in any portion of this application are herein expressly incorporated by reference in their entirety to the same extent as if each individual patent, application, or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one."

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used herein, all numerical values or ranges include fractions of the values and integers within such ranges and fractions of the integers within such ranges unless the context clearly indicates otherwise. A range is intended to include any sub-range therein, although that sub-range may not be explicitly designated herein. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 2-125 therefore includes 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, and 125, as well as sub-ranges within the greater range, e.g., for 2-125, sub-ranges include but are not limited to 2-50, 5-50, 10-60, 5-45, 15-60, 10-40, 15-30, 2-85, 5-85, 20-75, 5-70, 10-70, 28-70, 14-56, 2-100, 5-100, 10-100, 5-90, 15-100, 10-75, 5-40, 2-105, 5-105, 100-95, 4-78, 15-65, 18-88, and 12-56. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, a range of 1-1,000 includes, for example, 1-10, 10-20, 20-30, 30-40, 40-50, 50-60, 60-75, 75-100, 100-150, 150-200, 200-250, 250-300, 300-400, 400-500, 500-750, 750-1,000, and includes ranges of 1-20, 10-50, 50-100, 100-500, and 500-1,000. The range 100 units to 2000 units therefore refers to and includes all values or ranges of values of the units, and fractions of the values of the units and integers within said range, including for example, but not limited to 100 units to 1000 units, 100 units to 500 units, 200 units to 1000 units, 300 units to 1500 units, 400 units to 2000 units, 500 units to 2000 units, 500 units to 1000 units, 250 units to 1750 units, 250 units to 1200 units, 750 units to 2000 units, 150 units to 1500 units, 100 units to 1250 units, and 800 units to 1200 units. Any two values within the range of about 100 units to about 2000 units therefore can be used to set the lower and upper boundaries of a range in accordance with the embodiments of the present disclosure. More particularly, a range of 10-12 units includes, for example, 10, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, and 12.0, and all values or ranges of values of the units, and fractions of the values of the units and integers within said range, and ranges which combine the values of the boundaries of different ranges within the series, e.g., 10.1 to 11.5. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1).

The terms "increase," "increasing," "enhancing," or "enhancement" are defined as indicating a result that is greater in magnitude than a control number derived from analysis of a cohort, for example, the result can be a positive change of at least 5%, 10%, 20%, 30%, 40%, 50%, 80%, 100%, 200%, 300% or even more in comparison with the control number. Similarly, the terms "decrease," "decreasing," "lessening," or "reduction" are defined as indicating a result that is lesser in magnitude than a control number, for example, the result can be a negative change of at least 5%, 10%, 20%, 30%, 40%, 50%, 80%, 100%, 200%, 300% or even more in comparison with the control number.

As used in this specification and claims, the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" or "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The terms "about" or "approximately," where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment. Further, all references to one or more embodiments or examples are to be construed as non-limiting to the claims.

As used herein, "pure" or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90%

(w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Where used herein, the term "thick cell suspension" refers to a cell suspension comprising a cell density in a range of about $5\times10^8$ cells/ml to about $5\times10^9$ cells/ml.

Use of the word "we," "us," and/or "our" as a pronoun in the present disclosure refers generally to laboratory personnel, technicians, or other contributors who assisted in laboratory procedures and data collection and is not intended to represent an inventorship role by said laboratory personnel, technicians, or other contributors in any subject matter disclosed herein.

Certain of the disclosed compounds may exist in various stereoisomeric forms. Stereoisomers are compounds that differ only in their spatial arrangement. Enantiomers are pairs of stereoisomers that are non-superimposable mirror images of one another, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. Compounds of the present disclosure may contain one or more asymmetrically-substituted carbon or nitrogen atoms and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some non-limiting embodiments, a single diastereomer is obtained. The chiral centers of the compounds of the present disclosure can have the S or the R configuration.

Chemical formulas used to represent compounds of the present disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Particular examples of cationic ions of the crotonate, benzoate, and formate salts which may be used in the various embodiments of the present disclosure include, but are not limited to, sodium, potassium, and lithium. Particular examples of the crotonate, benzoate, and formate salts that may be used in the various embodiments of the present disclosure include, but are not limited to, sodium crotonate, sodium benzoate, sodium formate, potassium crotonate, potassium benzoate, potassium formate, lithium crotonate, lithium benzoate, and lithium formate, and these crotonate, benzoate, and formate salts of sodium, potassium, and lithium in any combination.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

Chemical Group Definitions

When used in the context of a chemical group: "hydrogen" is —H; "deuterium" is —D; "hydroxy" means —OH; "borane" is —B; "oxo" is =O; "carbonyl" is —C(=O)—; "carboxy" is —C(=O)OH (also written as —COOH or —$CO_2H$); the term "halogen" includes fluoro (fluorine, F), chloro (chlorine, Cl), bromo (bromine, Br), and iodo (iodine, I), "halo" means independently —F, —Cl, —Br or —I; "amino" is —$NH_2$; "hydroxyamino" is —NHOH; "nitro" is —$NO_2$; imino is =NH; "cyano" is —CN; "isocyanate" is —N=C=O; "azido" is —$N_3$; in a monovalent context "phosphate" is —OP(O)$(OH)_2$ or a deprotonated form thereof; in a divalent context "phosphate" is —OP(O)(OH)O— or a deprotonated form thereof; "mercapto" is —SH; "thio" is =S; "sulfonyl" is —$S(O)_2$—; and "sulfinyl" is —S(O)—.

EXAMPLES

The inventive concepts of the present disclosure will now be discussed in terms of several specific, non-limiting, examples. The examples described below, which include particular embodiments, will serve to illustrate the practice of the present disclosure, it being understood that the particulars shown are by way of example and for purposes of illustrative discussion of particular embodiments of the present disclosure only and are presented in the cause of providing what is believed to be a useful and readily understood description of procedures as well as of the principles and conceptual aspects of the inventive concepts.

Methods

Media Preparation

A basal medium was used initially to grow *S. aciditrophicus* anaerobically. The basal medium comprised various minerals, metals, vitamins, a cysteine-sodium sulfide reductant and sodium bicarbonate as the buffer with an 80% $N_2$:20% $CO_2$ gas phase (Table A; compositions of specific solution components are shown in Tables C-F below). The pH of the medium was adjusted to 7.1 to 7.3. The medium was boiled under oxygen-free 80% $N_2$:20% $CO_2$ gas mixture and, after cooling, sodium bicarbonate was added. The medium was dispensed in 10 ml amounts into serum tubes which were flushed with above anaerobic gas by inserting a gassing needle into the tube. The tubes were stoppered, crimp sealed, and autoclaved. The concentration of crotonate and other amendments are given in the tables and figures below.

TABLE A

Composition of basal medium with crotonate

| Component* | Amount (ml or grams) per liter |
|---|---|
| RST mineral solution | 10 ml |
| RST trace metal solution | 2.5 ml |
| RST vitamin solution | 10 ml |
| Resazurin (0.1% solution) | 1 ml |
| CA (to give 20 mM in medium) | 1.72 g |
| Sodium bicarbonate | 3.5 g |
| 2.5% cysteine-sulfide solution | 20 ml |
| Deionized water | Bring to 1 liter |

*Place about one-half the volume of water needed, then add the above solutions in the order listed, mixing the medium after each addition. Bring the pH to 7.1 to 7.3 with 10N NaOH after the addition of crotonic acid. Boil under an 80% $N_2$: 20% $CO_2$ gas phase and then cool. Add sodium bicarbonate and mix. Dispense into serum tubes under an 80% $N_2$: 20% $CO_2$ gas phase, stopper, crimp seal, and autoclave.

A basal lacking substrate (e.g., lacking crotonate), vitamins, and ammonium chloride is shown in Table B.

TABLE B

Composition of basal medium lacking substrate, vitamins and ammonium chloride

| Component* | Amount (ml or grams) per liter |
|---|---|
| NaCl | 0.8 g |
| KCl | 0.1 g |
| $KH_2PO_4$ | 0.1 g |
| $MgSO_4$•$7H_2$ | 0.2 g |
| $CaCl_2$•$2H_2O$ | 0.04 g |
| RST trace metal solution | 2.5 ml |
| Resazurin (0.1% solution) | 1 ml |
| Sodium bicarbonate | 3.5 g |
| 2.5% cysteine-sulfide solution | 20 ml |
| Deionized water | Bring to 1 liter |

*Place about one-half the volume of water needed, then add the above solutions in the order listed, mixing the medium after each addition. Bring the pH to 7.1 to 7.3 with 10N NaOH, then bring medium to 880 ml with deionized water. Cover top and sterilize. After cooling, bubble with sterile 80% $N_2$: 20% $CO_2$ gas phase for 30 min using a gassing probe with sterile filter attached. Then add 100 ml of a sterile sodium bicarbonate solution (3.5 g in 100 ml) and 20 ml of sterile 2.5% cysteine-sulfide solution and mix while still bubbling with sterile 80% $N_2$: 20% $CO_2$ gas phase. Stopper medium bottle with sterile stopper and remove gassing probe. Place serum tubes in the anaerobic chamber for several days, then stopper and crimp seal them and bring the tubes out and sterilize. Dispense 3.9 ml of the basal medium basal medium lacking substrate, vitamins and ammonium chloride into the capped, sterile serum tubes using degassed needles and syringes. Boil under an 80% $N_2$: 20% $CO_2$ gas phase and then cool.

Stock solutions of co-substrates and other compounds to enhance CHC formation were prepared as above for media preparation. The concentration of the stock solution was adjusted so that the addition of 0.1 ml of the solution gave a final concentration of 10 mM. For acids, sufficient 10 N NaOH was added to bring the pH to 7.0. The stock solution was boiled under anaerobic gas as above, cooled, and then dispensed into serum tubes sparged with an anaerobic gas. The stock solution tubes were stoppered, crimp sealed, and autoclaved.

To determine if *S. aciditrophicus* could grow without using sulfide as a reducing agent, different reducing solutions were made: 5% cysteine, 2.5% cysteine-2.5% sulfide (our normal reducing solution), 2.5% cysteine-1.0% sulfide, 2.5% cysteine-0.5% sulfide, 2.5% cysteine-0.2% sulfide and 2.5% cysteine-0.1% sulfide. Basal medium with each of the above reducing solutions was prepared and dispensed in 10-ml amounts into serum tubes as described above.

Additions of stock solutions or inoculum to and the removal of samples from sterile, anoxic medium were done using sterile syringes and needles that had been degassed with $O_2$-free 100% $N_2$. A sterile glass syringe filled with cotton and fitted with a metal canula (needle) provided the anaerobic sterile gas. The needle of the syringe used for additions or sampling was placed inside of the canula and flushed 5-10 times in the gas stream. A small amount of sterile anoxic gas is drawn into the needle, which is expelled immediately before inserting the needle into the stopper. The stopper of the culture was flame sterilized prior to inserting the needle.

For each condition, duplicate or triplicate tubes were used with 10 ml of sterile, anaerobic medium per tube. The tubes were each inoculated with 1 ml of a pure culture of *S. aciditrophicus* grown in the same medium with 20 mM crotonate to about mid-log phase of growth (absorbance at 600 nm of around 0.7 to 0.8). After inoculation, the absorbance of each culture was measured by placing the tube in the holder of a Spectronic 20D spectrophotometer. The spectrophotometer was blanked with a tube of uninoculated medium. The cultures were then incubated at 37° C. The absorbances of each culture was measured periodically (every two to three days) until no further increase in absorbance was detected. After growth has ceased, 1 ml was withdrawn from each tube. The pH of the sample was immediately measured by placing a drop on pH paper. The rest of the sample was placed in a microfuge tube, centrifuged in a microfuge to remove cells, and then frozen at −20° C. until analyzed by high-pressure liquid chromatography.

Washed-Cell Suspensions

Washed cell suspensions of *S. aciditrophicus* were prepared from about 9 liters of cells grown on 30 mM crotonate (about 1.5 liter per bottle) for the first experiment and from 5.2 liters of crotonate-grown *S. aciditrophicus* for the second experiment. *S. aciditrophicus* was grown on sodium crotonate in 1.5-liter volumes. Cells were harvested anaerobically in late log phase via centrifugation (14,300×g for 20 minutes at 24° C.). Plastic centrifuge tubes and bottles with rubber gaskets that had been in the anaerobic chamber were used. The culture bottles were brought inside of the anaerobic chamber, opened, and then pour into the centrifuge tubes or bottles. The centrifuge tubes or bottles were placed inside of a rotor and centrifuged. After centrifuging, the tubes or bottles were brought inside of the anaerobic chamber, opened, and the culture fluid was decanted. The cell pellets were suspended in 50 mM anoxic potassium phosphate buffer (pH of 7.0) which was reduced with 2.5% cysteine-sulfide solution. The resuspended pellets were centrifuged as above, and this procedure was repeated twice so that the pellet had been washed three times. The final pellet was resuspended in 25 ml of basal medium lacking substrate, vitamins, and ammonium chloride and incubated at 37° C.

Serum tubes with 3.9 ml of anoxic basal medium lacking substrate, vitamins and ammonium chloride were prepared. The tubes were first placed in the anaerobic chamber for several days, then stoppered and crimp sealed and brought out to the lab bench. The basal medium lacking substrate, vitamins and ammonium chloride was added via degassed needles and syringes. To these tubes, 0.1 ml of solutions of crotonate, formate, and/or benzoate were added from anoxic stock solutions to give the concentrations listed in the tables. Various amounts of the washed cell suspension were added to the tubes as indicated in the tables. The tubes were incubated at 37° C. For the first cell suspension experiment, samples were taken after 23 hours of incubation, then formate was added to certain tubes, and the suspensions were re-incubated. The final sample was taken after 63 hours of incubation. The second cell suspension experiment was sampled after 24 hours of incubation.

HPLC Analysis

Samples were microfuged at 17,900×g for 5 min at room temperature to remove cell material and stored at −20° C. until analysis. A Prevail Organic Acid (OA) (5 μm) (4.6×250 mm), with a guard cartridge of Prevail Organic Acid (OA) (5 μm) (4.6×7.5 mm) was used. These were purchased from W.R. Grace (Discovery Sciences) (Note: W.R. Grace sold this product line to HiChrom Ltd. in 2016). The mobile phase was 60% 25 mM potassium phosphate (pH 2.5):40% acetonitrile. The flow rate was 1 ml/min, and the sampling loop size was 20 μl. Crotonate and benzoate were detected at 254 nm and CHC and 1ΔCHC were detected at 214 nm. The above compounds were detected by matching retention times to those of known standards. The compounds were quantified by comparing the peak area of the eluting compound to a standard curve constructed from the peak areas of known standards. Internal standards show little inference, about 90 to 95% of the CHC added to a sample is detected.

Compositions of Media and Solutions

TABLE C

| Crotonate medium | |
|---|---|
| Component | per L |
| RST mineral solution | 10 ml |
| RST trace metal solution | 2.5 ml |
| RST vitamin solution | 10 ml |
| resazurin (0.1% solution) | 1 ml |
| 1.72 g CA for 20 mM crotonate | |
| 2.58 g CA for 30 mM crotonate | |
| 5.17 g CA for 60 mM crotonate | |
| 7.75 g CA for 90 mM crotonate | |
| 10.3 g CA for 120 mM crotonate | |
| 12.9 g CA for 150 mM crotonate | |

To the above mixtures, add deionized water to make 1 L. Adjust the pH to 7.1-7.3 with 10 N NaOH. Boil under 80% $N_2$/20% $CO_2$ or due a 5-min autoclave run, cool, and sparge with 80% $N_2$/20% $CO_2$. Add 3.5 g sodium bicarbonate. Dispense under 80% $N_2$/20% $CO_2$ into tubes or bottles (less than 130 ml volume). Stopper and crimp seal the tubes or bottles then autoclave.

As an alternative, after boiling and cooling of medium, place stopper on flask, tape shut, and bring into an anaerobic chamber. Dispense in anaerobic chamber, stopper, crimp seal, bring outside of chamber. Exchange headspace with 80% $N_2$/20% $CO_2$ then autoclave.

Reducing Solution

To make a 2.5% cysteine/2.5% sulfide reducing solution, combine NaOH (1.25 g), Cysteine·HCl (5 g), and $Na_2S \cdot 9H_2O$ (5 g) with distilled water (200 ml) according to the following steps. Use only clean, not discolored, sodium sulfide crystals. Rinse crystals in deionized water then blot dry. Weigh out cysteine·HCl and $Na_2S \cdot 9H_2O$ into separate containers, place a Kimwipe over top with rubber band and bring into anaerobic chamber (to prevent chemicals from spraying in the airlock during vacuum and sparging cycles). Add NaOH to water, boil under 100% $N_2$ gas phase, cool, stopper, bring into anaerobic chamber. Inside chamber, dissolve cysteine·HCl and then $Na_2S \cdot 9H_2O$ in degassed NaOH solution. Dispense, stopper, bring out of anaerobic chamber, crimp seal and autoclave. Wrap stopper of flask with tape to keep stopper on during vacuum-sparge cycles, make sure you fold over one end, so you get grip the tape easily inside of the chamber. Commercially available cysteine may be used as a substitute for cysteine·HCl. pH should be close to neutrality. The 5% cysteine·HCl solution is made as above without sulfide addition and using 2.5 g of NaOH. Cysteine·HCl must be neutralized prior to adding sulfide. If not neutralized, the acid will convert sulfide into toxic hydrogen sulfide gas.

Reduced Media

To make reduced media, add 20 ml of the 2.5% cysteine/2.5% sulfide reducing solution to the above crotonate media. The reducing solution can be added to cooled medium prior to dispensing, after dispensing, or after autoclaving. If added after autoclaving, the cysteine-sulfide solution must be anoxic and sterile. Adding the reducing solution after the tubes/bottles have been crimp sealed releases less sulfide into the air. If the medium will not be used within 2 days, it is best to add sterile, anoxic reductant 4 to 24 hours prior to inoculation.

Resazurin (0.1%) Solution

Add 0.1 g resazurin per 100 ml of distilled water.

TABLE D

| RST mineral solution* | |
|---|---|
| Component | g/l |
| NaCl | 80 |
| $NH_4Cl$ | 100 |
| KCl | 10 |
| $KH_2PO_4$ | 10 |
| $MgSO_4 \cdot 7H_2O$ | 20 |
| $CaCl_2 \cdot 2H_2O$ | 4 |

*Tanner, R. S. 1996. Cultivation of bacteria and fungi, pp. 52-60. In: C. J. Hurst, G. R. Knudsen, M. J. McInerney, L. D. Stezenbach, and M. V. Walter (ed.). 1996. *Manual for Environmental Microbiology*. American Society for Microbiology, Washington, D.C.

TABLE E

| RST trace metal solution* | |
|---|---|
| Component | g/l |
| nitrilotriacetic acid | 2.0 |
| adjust pH to 6.0 with KOH | |
| $MnSO_4 \cdot H_2O$ | 1.0 |
| $Fe(NH_4)_2(SO_4) \cdot 6H_2O$ | 0.8 |
| $CoCl_2 \cdot 6H_2O$ | 0.2 |
| $ZnSO_4 \cdot 7H_2O$ | 0.2 |
| $CuCl_2 \cdot 2H_2O$ | 0.02 |
| $NiCl_2 \cdot 6H_2O$ | 0.02 |
| $Na_2MoO_4 \cdot 2H_2O$ | 0.02 |
| $Na_2SeO_4$ | 0.02 |
| $Na_2WO_4$ | 0.02 |

Tanner, R. S. et al, 1996 (op. cit). Add about ½ of the deionized water to a flask and add components in the order listed. Bring to volume after all components are added.

TABLE F

| RST vitamin solution* | |
|---|---|
| Component | mg/l |
| pyridoxine-HCl | 10 |
| thiamine-HCl | 5 |
| riboflavin | 5 |
| calcium pantothenate | 5 |
| thioctic acid | 5 |
| Para-aminobenzoic acid | 5 |
| nicotinic acid | 5 |
| vitamin $B_{12}$ | 5 |
| MESA | 5 |

TABLE F-continued

| RST vitamin solution* | |
|---|---|
| Component | mg/l |
| biotin | 2 |
| folic acid | 2 |

Tanner, R. S. et al, 1996 (op. cit). MESA is required by some methanogens as a vitamin. It is probably not needed for the growth of *S. aciditrophicus* and can be omitted.

Results

Effect of High Crotonate Concentrations on Cyclohexane-1-Carboxylate Concentration Growing *S. aciditrophicus* in medium with high sodium crotonate concentrations resulted in high CHC concentrations (Table 1). Cultures with 120 and 150 mM crotonate had very high CHC concentrations of 11 to 13 mM or 1.4 to 1.7 g/L, which is well above the target concentration of 1 g/L (7.8 mM). The ratio of crotonate used per CHC formed for these two cultures was much higher than the established stoichiometry of 6 crotonate per one CHC, suggesting products other than CHC were formed. However, this initial finding could not be repeated. A second attempt using crotonate concentrations of 60, 90, and 120 mM resulted in CHC concentrations of 3.4±0.8, 3.3±0.9 and 4.0±1.1 mM, respectively. A third attempt was made with increasing concentrations of potassium crotonate (Table 2). Our thinking was that high sodium concentrations along with the large amounts of acetate produced maybe inhibitory. Cultures with 90 and 120 mM crotonate had CHC concentrations above 6 mM or 0.8 g/L, which are close to the target value of 7.8 mM or 1 g/L. The CHC concentrations detected in cultures with potassium crotonate were lower than the maximum values reported in our initial experiment.

TABLE 1

Effects of different sodium crotonate concentrations on the production of CHC.

| Crotonate (mM) | $A_{600}$ | CHC (mM) | CHC (g/L) | 1ΔCHC (mM) | Crotonate used (mM) | Crotonate to CHC ratio |
|---|---|---|---|---|---|---|
| 20 | 0.7 | 2.0 | 0.26 | 0.7 | Not done | Not done |
| 60 | 1.1 | 4.0 | 0.5 | 0.9 | 46 | 7.6 |
| 90 | 1.1 | 6.9 | 0.9 | 0.9 | 71 | 12 |
| 120 | 1.0 | 13.3 | 1.7 | 0.9 | 95 | 16 |
| 150 | 0.7 | 11.4 | 1.4 | 0.9 | 123 | 20 |

CHC = cyclohexane-1-carboxylate; 1ΔCHC = cyclohex-1-ene-1-carboxylate.

TABLE 2

Effects of different potassium crotonate concentrations on the production of CHC.

| Crotonate (mM) | Sample A (mM) | Sample B (mM) | Average CHC (mM) | CHC (g/L) |
|---|---|---|---|---|
| 30 | 3.0 | 2.4 | 2.7 | 0.35 |
| 60 | 6.1 | 4.8 | 5.4 | 0.70 |
| 90 | 6.9 | 6.4 | 6.6 | 0.85 |
| 120 | 6.8 | 6.1 | 6.5 | 0.83 |
| 150 | 5.7 | 5.0 | 5.3 | 0.68 |

CHC = cyclohexane-1-carboxylate; 1ΔCHC = cyclohex-1-ene-1-carboxylate.

High CHC Concentrations are Produced with Benzoate as Electron Acceptor

*S. aciditrophicus* was grown in medium with 30 mM crotonate at different benzoate concentrations (0, 2.5, 5, 7.5, and 10 mM). *S. aciditrophicus* was also grown in medium with 30 mM crotonate and 5, 10, 15 and, 20 mM formate. At each formate concentration, tubes of media with benzoate concentrations of 0, 2.5, 5, 7.5, and 10 mM were prepared. Each condition was done in duplicate.

Cultures that contained 30 mM crotonate and 10 mM benzoate produced CHC concentrations ranging from 8 to 9 mM regardless of whether formate was present or not (Table 3). One culture with 30 mM crotonate and 7.5 mM benzoate, but without formate, produced 7 mM CHC. However, a culture with 30 mM crotonate, 7.5 mM benzoate, and 5 mM formate produced 8.6 mM CHC. Most likely, benzoate was being used as an electron acceptor and was reduced to CHC using electrons derived from crotonate oxidation. The addition of formate as an additional electron donor did not markedly increase CHC concentration. Also, the addition of formate severely affected growth as discussed in the following section.

Cultures with 7.5 mM or 10 mM benzoate, 5 mM formate, and 30 mM crotonate had CHC concentrations above the target value (Table 3). None of the cultures with 10, 15 or, 20 mM formate grew regardless of whether benzoate was present or not. These cultures were not analyzed for CHC production.

TABLE 3

CHC production by *S. aciditrophicus*. grown with 30 crotonate with and without 5 mM formate at different benzoate concentrations (0, 2.5, 5, 7.5 and 10 mM)

| Formate added (mM) | Benzoate added (mM) | CHC made (mM) Replicate A | CHC made (mM) Replicate B |
|---|---|---|---|
| 0 | 0 | 2.5 | 2.2 |
| | 2.5 | 3.5 | 3.0 |
| | 5 | 3.0 | 2.3 |
| | 7.5 | 7 | 3.1 |
| | 10 | 9 | 8.2 |
| 5 | 0 | 3.0 | 2.1 |
| | 2.5 | 3.4 | 5.8 |
| | 5 | 3.9 | |
| | 7.5 | 8.6 | 5.8 |
| | 10 | 9 | 8 |

*S. aciditrophicus* was grown with 30 crotonate with and without 5 mM formate at different benzoate concentrations (0, 2.5, 5, 7.5 and 10 mM).

Note:

The duplicate (tube B) of the 5 mM formate + 5 mM benzoate grew much faster than any of the other tubes containing formate. Its growth was about the same as the 5 mM benzoate tubes lacking formate. It is likely that formate was not added to the tube, so this tube has been omitted from these analyses. Tube A containing 5 mM formate and 0 mM benzoate did not grow during 63 days of incubation, but the tube was turbid after another month of incubation, so it was analyzed.

Figure 2:
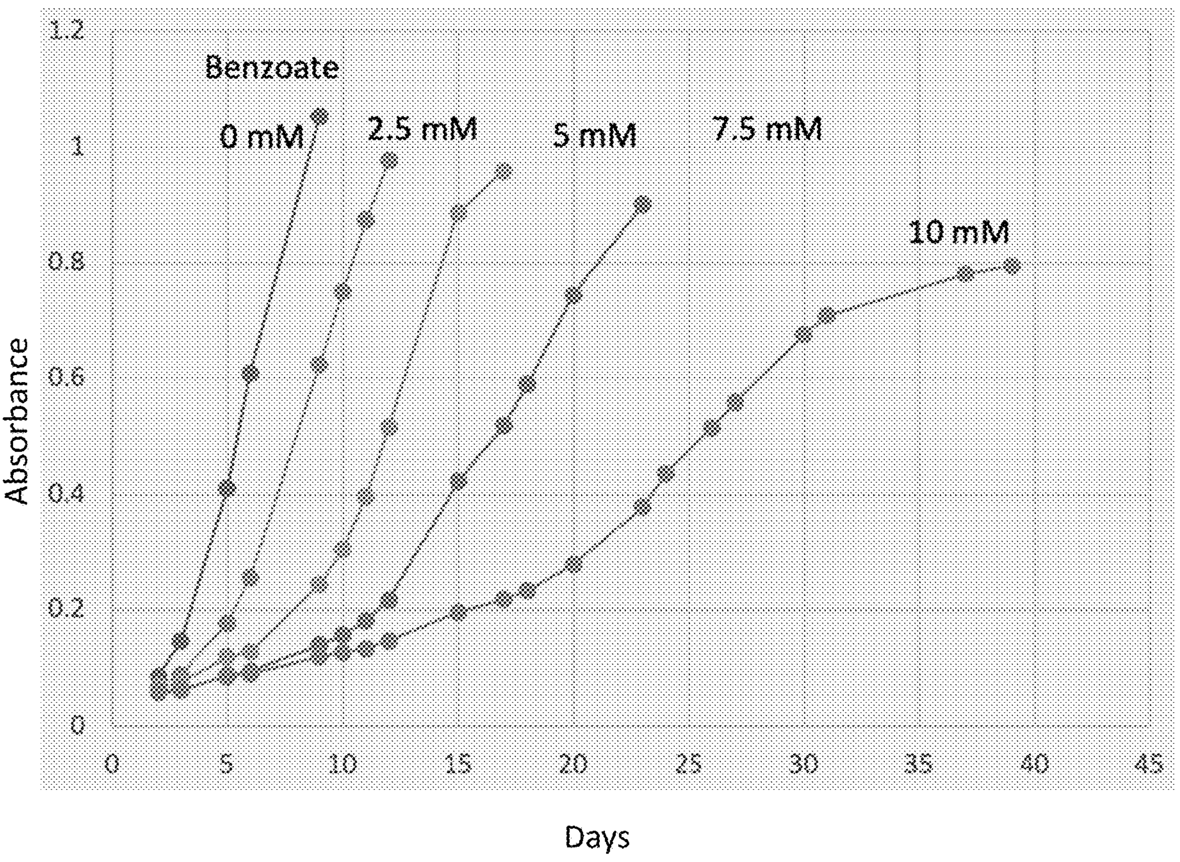
FIG. 2 shows the growth of *S. aciditrophicus* cultures with 30 mM crotonate and different benzoate concentrations without formate.
Figure 3:
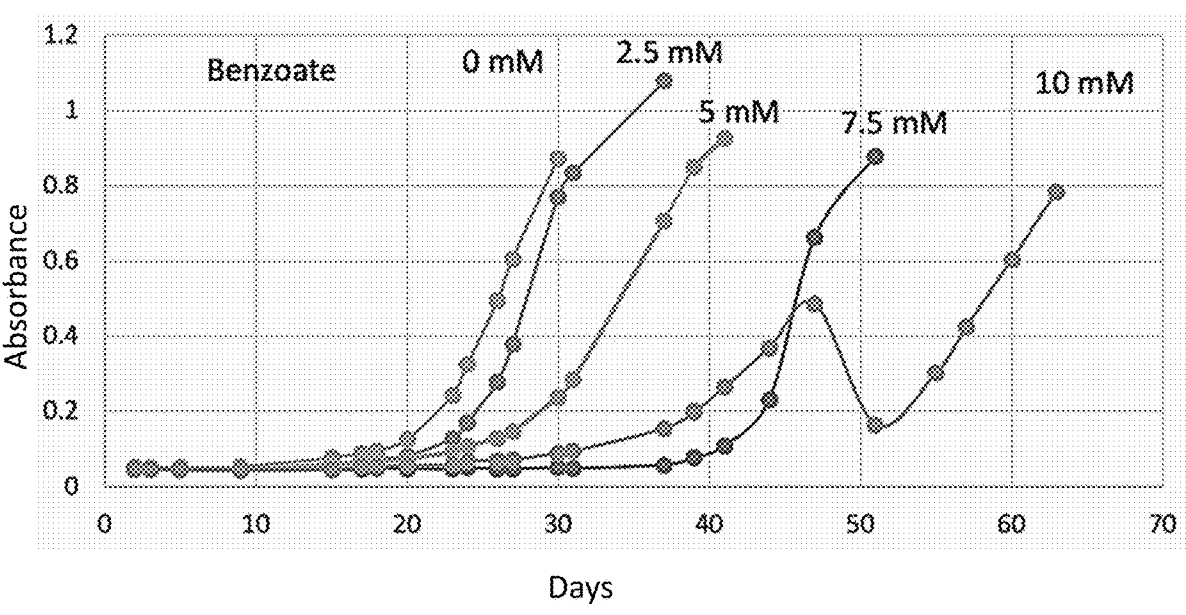
FIG. 3 shows the growth of *S. aciditrophicus* cultures with 30 mM crotonate, 5 mm formate, and different benzoate concentrations.

The presence of benzoate increased the lag time before growth commenced and slowed the growth rate (FIG. 2). Cultures with 30 mM crotonate and 10 mM benzoate took 30-40 days to reach maximum absorbance. Additionally, the presence of formate greatly increased the lag time before growth commenced and slowed the rate of growth (FIG. 3). Little or no growth was observed in cultures with formate until 20 days of incubation. The presence of formate did not markedly increase CHC concentration but negatively impacted growth.

CHC Production with Multiple Additions of Crotonate or Benzoate After Growth Commences The above experiments where *S. aciditrophicus* was grown in medium with both crotonate and benzoate resulted in more CHC production than in cultures where *S. aciditrophicus* was grown in medium with only crotonate (Table 3). However, growth was severely impaired when benzoate was present at the time of inoculation. We hypothesized that the presence of benzoate at the time of inoculation inhibited growth and CHC production because the cell concentration was low. To test this hypothesis, we grew *S. aciditrophicus* in medium with 30 mM crotonate to about mid-log phase of growth and then added 5 mM benzoate at day 4 and day 10. As a control, we grew another set of cultures in medium with 30 mM crotonate to about mid-log phase of growth and added 30 mM crotonate at day 4 and day 7 (Table 4).

Cultures that received multiple additions of crotonate produced 1.9±0.1 mM CHC after 10 days of incubation (Table 4). Of the 90 mM crotonate that was added, 52 mM was used, which should have resulted in the production of about 8.9 mM CHC according to equation 1. The cultures that received multiple additions of benzoate produced twice the amount of CHC (4.9±0.4 mM) than those that received multiple crotonate additions (Table 4). During day 4 to day 10, 4.3±05 mM benzoate was used and 4.1 mM CHC was made, which suggests that benzoate was being reduced to CHC.

TABLE 4

CHC production by *S. aciditrophicus* grown with multiple additions of crotonate or benzoate.*

Cultures that received multiple crotonate additions

| Days | Crotonate added (mM) | Benzoate added (mM) | Crotonate used (mM) | CHC made (mM) |
|---|---|---|---|---|
| 0 | 31.4 ± 2 | 0 | 0 | |
| 4 | 30 | 0 | 10.3 | 0.5 ± 0.1 |
| 7 | 30 | 0 | 23.9 | 1.2 ± 0.1 |
| 10 | 0 | 0 | 53.0 | 1.9 ± 0.1 |

Cultures that received multiple benzoate additions

| Days | Crotonate added (mM) | Benzoate added (mM) | Crotonate used (mM) | CHC made (mM) | Benzoate used (mM) |
|---|---|---|---|---|---|
| 0 | 31.4 | | 0 | | |
| 4 | | 5 | 10.2 | 0.2 ± 0.1 | |
| 10 | | 5 | 21.1 | 4.3 ± 0.5 | 4.8 |
| 12 | | | 22.5 | 4.9 ± 0.4 | 7.1 |

*One set of cultures received additions of crotonate after 4 and 7 days of incubation to increase the crotonate concentration by 30 mM crotonate after each addition. The other set of cultures received additions of benzoate to increase the benzoate concentration by 5 mM after each addition. Data are from triplicate cultures.

Figure 4:
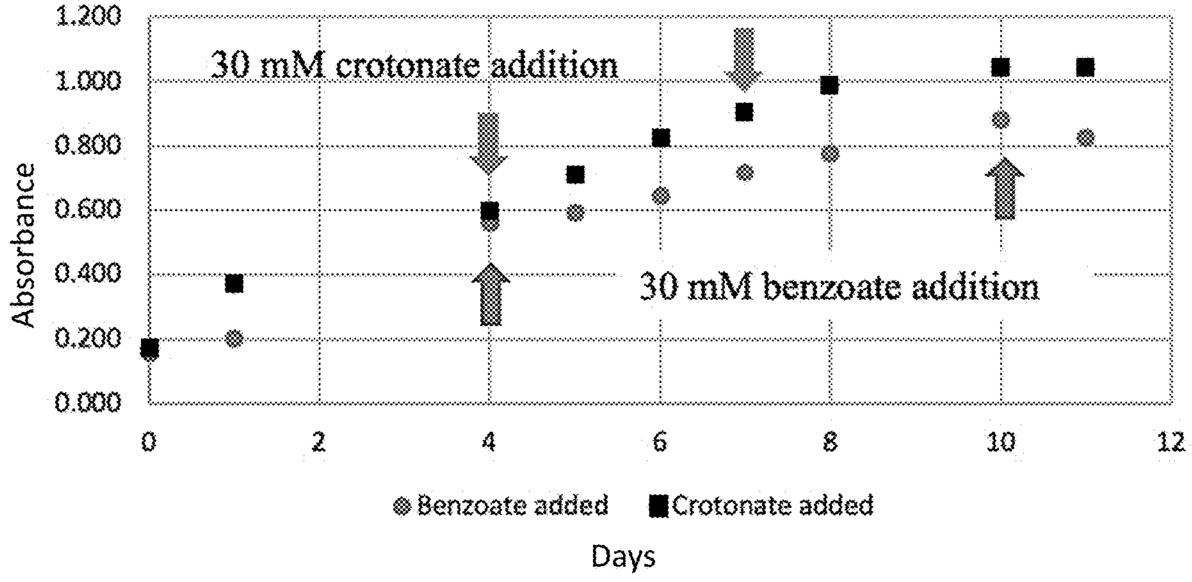
FIG. 4 shows the growth of *S. aciditrophicus* cultures in medium with 30 mM crotonate that received multiple crotonate or benzoate additions.

Cultures that received multiple crotonate reached their maximum absorbance at day 10 (A660 of 1.0) while cultures that received multiple benzoate additions reached a maximum absorbance of 0.89 at day 10 (FIG. 4). Both sets of cultures reached about the same absorbance at day 4 (0.59 versus 0.56, respectively) (FIG. 3) prior to additions being made. After day 4, cultures that received benzoate had a slower growth rate than those that received additional crotonate (FIG. 4).

The addition of benzoate at day 4 prevented the long lag period (about 10 days) that was observed in cultures that had 5 mM benzoate at the time of inoculation (FIG. 3). Additionally, the cultures that received benzoate at day 4 and day 10 made 4.9 mM benzoate after 12 days of incubation compared to 3 mM benzoate made after 40 days of incubation in cultures that had 5 mM benzoate at the time of inoculation (Table 3 and Table 4).

CHC Production by Washed Cell Suspensions of *S. aciditrophicus*

Washed-cell suspensions of *S. aciditrophicus* were prepared from about 9 liters of cells grown on 30 mM crotonate (about 1.5 liter per bottle). The cells were harvested anaerobically by centrifugation, washed with anoxic phosphate buffer with cysteine-sulfide reducing solution, and recentrifuged. The final pellet was resuspended in medium without ammonium chloride and vitamins. A number of variables were tested including concentrations of crotonate, formate and benzoate, the volume of cells added (1 to 4 ml), incubation time (23 or 63 hr) and dilution of the sample for HPLC analysis. Formate was added after 24 hours of incubation at 37° C. as indicated. Samples were taken prior to formate addition and after 63 hours of incubation. Due to the number of variables investigated, the data in Table 5 are single determinations.

All cell suspensions with crotonate and 10 mM benzoate had CHC concentrations that exceeded the target value of 7.8 mM after 24 hours of incubation (indicated in red in Table 5). The CHC concentration increased slightly in suspensions with 20 and 40 mM crotonate and 10 mM benzoate after 63 hours of incubation. This may have been due to the addition of formate after 24 hours. Formate serves as an additional source of electrons for benzoate reduction to CHC. The oxidation of 5 mM formate should result in the production of about 1.6 mM CHC. The observed increases in CHC concentration were less than that predicted. Formate addition did not increase CHC concentration in suspensions with 60 of 80 mM crotonate.

The addition of benzoate resulted in much higher CHC concentrations compared to suspensions with the same amount of crotonate but without benzoate added. When crotonate and benzoate were present, much less crotonate was used per CHC made. Without benzoate, about 9 to 12 crotonates were used per CHC made (theoretical value of 6:1 by crotonate fermentation; equation 1). With benzoate, about 2 to 6 crotonates were used per CHC made. Cell suspensions with 20 and 40 mM crotonate and 10 mM benzoate used from 2.2 to 3.7 crotonate per CHC made, which is close to the expected value for benzoate respiration of 3 crotonate per CHC made (equation 2). In suspensions with 60 and 80 mM crotonate and 10 mM benzoate, the crotonate to CHC ratio is much higher and close to that of CHC formed only by crotonate fermentation and not by benzoate reduction.

TABLE 5

CHC Production by Washed Cell Suspensions with Different Crotonate, Benzoate and Formate Concentrations. Blank cells mean that the compound was not added or sample not taken at 24 hours.

| Crotonate (mM) | Benzoate (mM) | Formate (mM) (added after 24 hr) | Dil. of sample | ml of cell susp. | CHC (mM) at 24 hr (before formate) | CHC (mM) at 63 hr (after formate) | CHC (g/L) at 63 hr (after formate) | Crotonate to CHC Ratio |
|---|---|---|---|---|---|---|---|---|
| 60 | | | 4 | 2 | 3.6 | 4.7 | 0.6 | 5.5 |
| 60 | | | 4 | 2 | | 2.4 | 0.3 | 25.4 |
| 60 | | 2.5 | 10 | 2 | 2.0 | 1.7 | 0.2 | 24.4 |

TABLE 5-continued

CHC Production by Washed Cell Suspensions with Different Crotonate, Benzoate and Formate Concentrations. Blank cells mean that the compound was not added or sample not taken at 24 hours.

| Crotonate (mM) | Benzoate (mM) | Formate (mM) (added after 24 hr) | Dil. of sample | ml of cell susp. | CHC (mM) at 24 hr (before formate) | CHC (mM) at 63 hr (after formate) | CHC (g/L) at 63 hr (after formate) | Crotonate to CHC Ratio |
|---|---|---|---|---|---|---|---|---|
| 60 | | 2.5 | 2 | 2 | | 4.1 | 0.5 | 10.4 |
| 60 | 5 | 5 | 2 | 2 | 4.8 | 2.7 | 0.3 | 13.8 |
| 60 | 5 | 5 | 3 | 2 | 3.6 | 2.8 | 0.3 | 13.1 |
| 20 | | | 4 | 1 | | 0.8 | 0.1 | 23.4 |
| 40 | | | 4 | 1 | | 3.3 | 0.4 | 10.7 |
| 60 | | | 4 | 1 | | 3.0 | 0.4 | 12.3 |
| 80 | | | 4 | 1 | | 2.6 | 0.3 | 15.4 |
| 20 | 0 | | 4 | 4 | | 2.0 | 0.3 | 9.5 |
| 40 | 0 | | 4 | 4 | | 3.4 | 0.4 | 12 |
| 60 | 0 | | 4 | 4 | | 4.1 | 0.5 | 9.1 |
| 80 | 0 | | 4 | 4 | | 4.3 | 0.6 | 10 |
| 20 | 10 | 5 | 4 | 4 | 7.8 | 8.4 | 1.1 | 2.2 |
| 40 | 10 | 5 | 4 | 4 | 7.9 | 8.3 | 1.1 | 3.7 |
| 60 | 10 | 5 | 4 | 4 | 8.2 | 7.9 | 1.0 | 5.3 |
| 80 | 10 | 5 | 4 | 4 | 7.8 | 7.5 | 1.0 | 6.1 |

With a second cell suspension, CHC concentration ranged from 6.4 to 6.6 when 10 mM benzoate and 20 to 60 mM crotonate were present (Table 6). Increasing the benzoate concentration to 15 or 20 mM slightly increased CHC concentration, with the highest CHC concentration of 7.7 mM obtained with 60 mM crotonate and 15 mM benzoate. Clearly, not all the benzoate is being reduced as 60 mM crotonate should be able to fully reduce 20 mM benzoate to CHC according to equation 2. It may be that CHC concentrations above 6 to 7 mM become inhibitory for *S. aciditrophicus*.

TABLE 6

CHC production with different crotonate and benzoate concentrations by a second cell suspension. Each reaction contained 1 ml of the cell suspension in 5 ml total reaction volume.

| Benzoate | CHC concentration (mM) at the following amounts of crotonate | | |
|---|---|---|---|
| (mM) | 20 mM | 40 mM | 60 mM |
| 0 | 2.7 | 3.1 | 4.4 |
| 10 | 6.5 | 6.6 | 6.4 |
| 15 | 7.1 | 6.9 | 7.7 |
| 20 | 6.1 | 7.0 | 6.7 |

Effect of Co-Substrates on CHC Formation

The effect of addition of a co-substrate on growth and CHC formation is shown in Table 7. The concentration of crotonate was intended to be 20 mM but after additions and inoculation, the actual concentration of crotonate as determined by HPLC analysis was 17.5 mM. According to equation 1, 17.5 mM crotonate should produce 2.9 mM CHC if all the crotonate was used.

The growth of *S. aciditrophicus* in media with glycerol or sugars added was about the same as in medium with only crotonate. The presence of most of the organic acids slightly inhibited growth with final absorbance about 0.1 unit less than in medium with only crotonate present. The presence of increasing amounts of benzoate led to decreases in the final absorbance while lactate or octanoate addition severely inhibited growth.

The addition of benzoate, hexanoate, hexenoate, and hydrogen gave CHC concentrations above 2 mM compared to 1.5 mM CHC produced in medium with only crotonate present. Subsequently we started measuring the amount of 1ΔCHC, which varied from about 0.5 to around 1 mM in cultures at the end of growth. The CHC concentration was 4.2 mM (0.54 g/L) when hexanoate was added as a co-substrate. This result appeared to be promising. However, when *S. aciditrophicus* cultures grown on hexenoate or hexanoate was transferred into the same medium, much less CHC was detected, 1.2 mM and 2.0 mM for hexenoate- and hexanoate-grown cultures respectively. Further experiments with different amounts of hexenoate and hexanoate (5, 10 and 15 mM) resulted in concentrations less than 2 mM CHC, except when 10 mM hexenoate was added (Table 8). The latter condition gave slightly more than 2 mM CHC.

As the pathway for crotonate metabolism is reversible, it was thought that the addition of high acetate concentrations would push carbon to CHC formation. However, this was not the case. The addition of 20 mM acetate or more resulted in CHC concentrations slightly greater than 2 mM CHC (Table 7). Increasing the acetate concentration did not result in proportional increase in CHC concentration and inhibited growth. High acetate concentrations are unlikely to achieve the target CHC concentration.

TABLE 7

Effects of co-substrates on CHC production and growth on *S. aciditrophicus*. The crotonate concentration was 17.5 mM after additions and inoculation.

| Additions | Crotonate (mM) | Co-Substrate (mM) | $A_{600}$ | CHC (mM) | 1ΔCHC (mM) |
|---|---|---|---|---|---|
| No addition | 20 | 0 | 0.77 | 1.50 | |
| Fructose | 20 | 10 | 0.82 | 1.73 | |
| Glucose | 20 | 10 | 0.82 | 1.69 | |
| Glycerol | 20 | 5 | 0.67 | 1.59 | |
| Sucrose | 20 | 10 | 0.82 | 1.73 | |
| Acetate | 20 | 10 | 0.74 | 1.26 | |
| Acetate | 20 | 20 | 0.7 | 2.0 | 0.6 |
| Acetate | 20 | 40 | 0.7 | 2.2 | 0.6 |
| Acetate | 20 | 60 | 0.6 | 2.0 | 0.7 |

TABLE 7-continued

Effects of co-substrates on CHC production and growth on *S. aciditrophicus*. The crotonate concentration was 17.5 mM after additions and inoculation.

| Additions | Crotonate (mM) | Co-Substrate (mM) | $A_{600}$ | CHC (mM) | 1ΔCHC (mM) |
|---|---|---|---|---|---|
| Acetate | 20 | 80 | 0.5 | 2.1 | 0.8 |
| Benzoate | 20 | 2.5 | 0.70 | 2.10 | |
| Benzoate | 20 | 5.0 | 0.48 | 2.18 | |
| Benzoate | 20 | 10 | 0.69 | 2.67 | |
| Butyrate | 20 | 10 | 0.57 | 1.41 | |
| Butyrate | 20 | 10 | 0.70 | 1.40 | 0.9 |
| Formate | 20 | 10 | 0.74 | 1.63 | |
| Fumarate | 20 | 10 | 0.69 | 1.44 | |
| Glutarate | 20 | 10 | 0.73 | 1.65 | |
| Hexenoate | 20 | 10 | 0.66 | 2.85 | |
| Hexanoate | 20 | 10 | 0.62 | 4.22 | |
| Hydrogen | 20 | 2.5 mL added | 0.68 | 2.16 | |
| Transfer of Hexenoate | 20 | 10 | 0.7 | 1.2 | 0.6 |
| Transfer of Hexanoate | 20 | 10 | 0.5 | 2.0 | 0.6 |
| Lactate | 20 | 10 | Poor growth | Not analyzed | |
| Malate | 20 | 10 | 0.71 | 1.46 | |
| Pimelic Acid | 20 | 10 | 0.7 | 2.0 | 0.5 |
| Octanoic Acid | 20 | 10 | 0.1 | Not detected | |
| Succinate | 20 | 10 | 0.68 | 1.51 | |

TABLE 8

The effect of different concentrations of hexenoate and hexanoate on growth and CHC concentration.

| Addition | Crotonate (mM) | Co-Substrate (mM) | $A_{600}$ | CHC (mM) |
|---|---|---|---|---|
| Hexenoate | 10 | 5 | 0.71 | 0.12 |
| Hexenoate | 10 | 10 | 0.64 | 2.17 |
| Hexenoate | 10 | 15 | 0.48 | 0.96 |
| Hexanoate | 10 | 5 | 0.69 | 0.28 |
| Hexanoate | 10 | 10 | 0.47 | 0.53 |
| Hexanoate | 10 | 15 | 0.21 | 0.15 |
| None | 20 | 0 | 0.7 | 2.0 |

CHC production in crotonate medium with complex growth factors added.

We tested the effect of adding complex growth factors such as molasses, casamino acids, yeast extract and trypticase (0.5% final concentration) on growth and CHC production by *S. aciditrophicus* (FIG. 4 and Table 9). We thought that *S. aciditrophicus* might be able to use the carbon in these complex materials for biosynthesis, which might spare crotonate carbon for CHC production. The growth of *S. aciditrophicus* in medium with various complex growth factors was about the same as in medium with only crotonate (Table 9). Only cultures with casamino acids had slightly less growth with a final absorbance of 0.9 compared to about 1.0 for the other conditions. The CHC concentration (5 mM) in cultures with yeast extract was twice that in cultures with any other addition or in the cultures that had only crotonate (Table 9).

TABLE 9

CHC production when *S. aciditrophicus* is grown with 20 mM crotonate and various complex growth added at 0.5% (5 grams or mls per liter) final concentration.

| Addition | CHC made (mM) | Crotonate used (mM) | OD after 12 days |
|---|---|---|---|
| None | 2.5 ± 0.2 | 24.6 ± 1.4 | 1.0 |
| Molasses | 2.1 ± 0.2 | | 1.0 |
| Casamino acids | 2.8 ± 0.3 | | 0.9 |
| Yeast extract | 5.0 ± 0.8 | 20.4 ± 3.6 | 1.0 |
| Trypticase | 2.4 ± 0.2 | | 1.0 |

Figure 5:
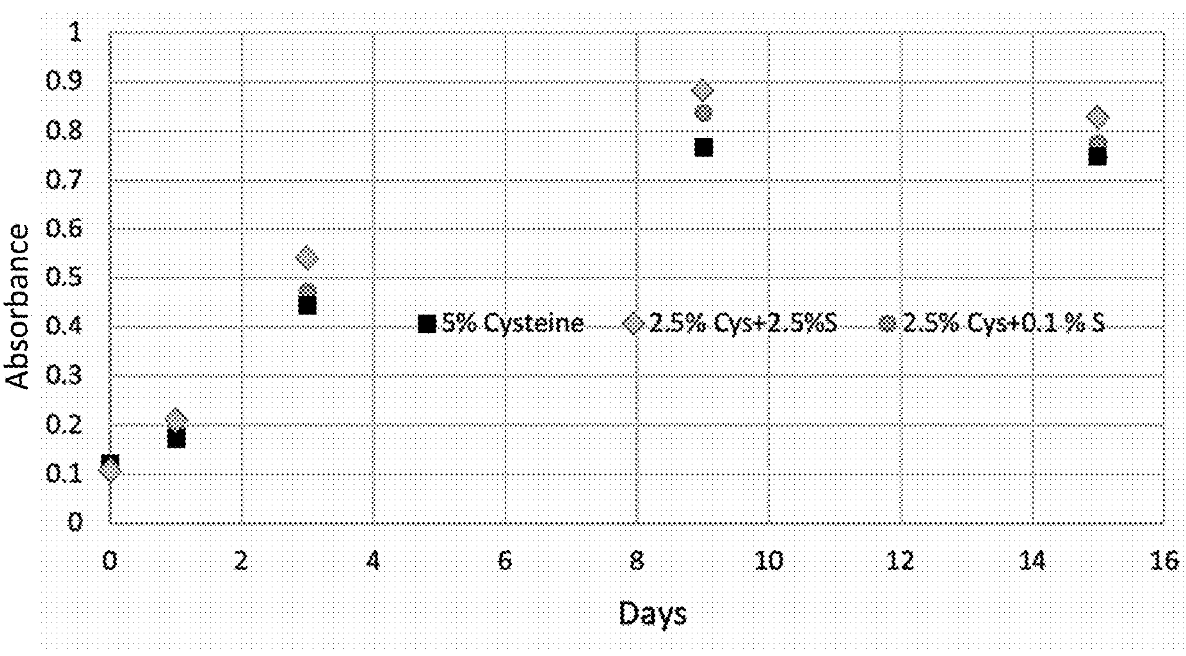
FIG. 5 shows the growth of *S. aciditrophicus* cultures in medium with and without sulfide.
Figure 6:
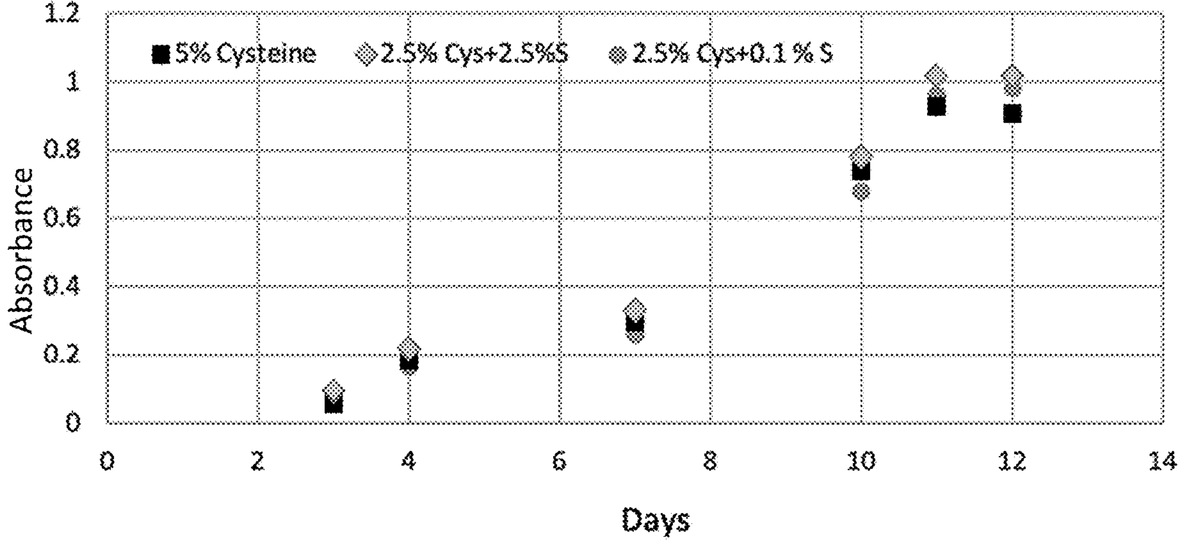
FIG. 6 shows the growth of *S. aciditrophicus* cultures after second transfer into medium with and without sulfide.

Growth of *S. aciditrophicus* with Only Cysteine as a Reductant or with Cysteine and Low Amounts of Sulfide as a Reductant We routinely grow *S. aciditrophicus* in medium that contains 20 ml per liter of a 2.5% cysteine-2.5% sulfide reducing solution. We tested whether *S. aciditrophicus* could grow in medium with only cysteine as the reductant (20 ml of 5% cysteine solution per liter) or with low amounts of sulfide (20 ml of 2.5% cysteine solution with 1.0% sulfide, 0.5% sulfide, 0.2% sulfide or 0.1% sulfide per liter). Cultures of *S. aciditrophicus* with only cysteine as the reductant (2 ml of 5% cysteine solution) grew at about the same rate and to about the same final absorbance as cultures that had our normal 2.5% cysteine-2.5% sulfide reducing solution or a reducing solution with 2.5% cysteine and lower amounts of sulfide (FIG. 5). (Data are shown only for cultures reduced with 5% cysteine solution, 2.5% cysteine-2.5% sulfide solution and 2.5% cysteine-0.1% sulfide solution). After growth, the cultures were transferred into medium of the same composition, i. e., the same reducing solution. Even after one transfer, there was no difference in growth between cultures that had only cysteine as the reductant compared to those that had cysteine and different amounts of sulfide (FIG. 6). Cultures grown with 5% cysteine as the reductant had a final CHC concentration of 1.9 mM while those grown with 2.5% cysteine-2.5 sulfide had a final CHC concentration of 2.0 mM. Thus, a reducing solution containing sulfide is not required. It is likely that *S. aciditrophicus* gets the sulfur needed for growth from cysteine or the small amounts of sulfide formed from the hydrolysis of cysteine.

In conclusion, a variety of additions to the growth medium and different crotonate concentrations were tested to determine if *Syntrophus aciditrophicus* could produce cyclohexane-1-carboxylate (CHC) in concentrations greater than 7.8 mM or 1 g/L. We found that growing *S. aciditrophicus* in medium with 90 mM or 120 mM potassium crotonate resulted in CHC concentration of 6.1 to 6.9 mM (0.83 to 0.85 g/L). Growing *S. aciditrophicus* in medium with 30 mM crotonate and 10 mM benzoate gave CHC concentration of 8.6 mM (1.1 g/L). In medium with 30 mM crotonate. 5 mM formate and 7.5 mM or 10 mM benzoate gave CHC concentrations of 7.2 and 8.5 mM (0.9 and 1.1 g/L), respectively. However, the presence of benzoate and formate inhibited growth, extending the time to reach stationary phase from about 5 days in medium with only crotonate to about 30 days in medium with benzoate and formate. To avoid the long lag times observed when benzoate was present at the time of inoculation, we grew *S. aciditrophicus* in medium with 30 mM crotonate to mid-log phase of growth and added 5 mM benzoate at day 4 and day 10. Cultures that received benzoate at days 4 and 10 produced 4.9 mM CHC after 12 days of incubation, which was much higher than the amount of CHC produced (1.9 mM) in control cultures that received additions of 30 mM crotonate at days 4 and 7. When *S. aciditrophicus* was grown in medium with 20 mM crotonate and yeast extract as a supplement. CHC concentration was 5.0±0.8 mM (0.64 g/L). This was a surprise as *S. aciditrophicus* is known to use only benzoate or crotonate for pure culture growth. The addition of various sugars, fatty acids, organic acids, or complex sources of amino acids or peptides did not increase CHC concentration above that in medium with only 20 mM crotonate (about 2 mM or less CHC produced). CHC concentration in medium with high potassium crotonate concentrations (90 mM and 120 mM) were about the same (6 to 7 mM), suggesting that CHC may be inhibitory as its concentration increases. In certain non-limiting embodiments, a method of producing CHC at a target value of at least 1 g/L is to grow *S. aciditrophicus* with crotonate and then add benzoate and possibly more crotonate when cell densities are high. e.g., when the mid-log phase of growth is reached. Alternatively. CHC can be made by cell suspensions containing crotonate and 5 to 10 mM benzoate. Another approach is to grow *S. aciditrophicus* in a medium with various combinations of crotonate and yeast extract with or without benzoate additions.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A method of producing cyclohexane-1-carboxylate (CHC), comprising the steps of:

providing a growth medium comprising a yeast extract and a crotonate salt;

providing a culture of *Syntrophus aciditrophicus* (*S. aciditrophicus*);

using the growth medium to initiate growth of the culture of *S. aciditrophicus;* after the *S. aciditrophicus* has initiated cell division, adding a benzoate salt to the growth medium;

culturing the *S. aciditrophicus* for an incubation period; and after the incubation period, purifying from the growth medium the CHC produced in the growth medium during the incubation period, wherein the amount of CHC in the growth medium has achieved a concentration of at least 1 g/l (7.8 mM).

2. The method of claim 1, wherein the crotonate salt is sodium crotonate.

3. The method of claim 1, wherein the crotonate salt is potassium crotonate.

4. The method of claim 1, wherein the yeast extract is provided in a concentration of at least about 5 grams per liter, the crotonate salt is provided in a concentration of at least about 30 mM, and the benzoate salt is provided in a concentration of at least about 5 mM.

5. The method claim 1, wherein the crotonate salt is in a concentration of at least about 60 mM.

6. The method of claim 1, wherein the benzoate salt is added when the absorbance of the *S. aciditrophicus* reaches about 0.3 units at 600 nM.

7. The method of claim 1, wherein the benzoate salt is added about 24 to about 96 hours after initiation of growth of the *S. aciditrophicus.*

8. The method of claim 1, wherein the benzoate salt is added when the absorbance of the *S. aciditrophicus* reaches about 0.3 units at 600 nM and about 24 to about 96 hours after initiation of growth of the *S. aciditrophicus.*

9. The method of claim 1, wherein the benzoate salt has a concentration in a range of about 5 mM to about 20 mM.

10. The method of claim 1, further comprising adding additional benzoate at a concentration of 1 to 2 mM each day after the absorbance of the *S. aciditrophicus* reaches about 0.3 units at 600 nanometers.

11. The method of claim 1, wherein the growth medium further comprises a formate salt of at least about 5 mM concentration.

12. The method of claim 1, wherein the yeast extract has a concentration in a range of about 5 g/l to about 15 g/l.

13. A method of producing cyclohexane-1-carboxylate (CHC), comprising the steps of:

(a) providing a growth medium comprising a crotonate salt in a concentration of at least about 30 mM;

(b) using the growth medium to grow a culture of *Syntrophus aciditrophicus* (*S. aciditrophicus*);

(c) collecting cells of the culture of *S. aciditrophicus* by centrifugation;

(d) resuspending the cells in an anoxic potassium phosphate buffer;

(e) repeating steps (c) and (d) until the cells have been washed at least three times;

(f) after step (e), forming a cell suspension by resuspending the cells in a first basal medium lacking crotonate salt and benzoate, vitamins, and ammonium chloride;

(g) providing a modified basal medium comprising first basal medium combined with crotonate salt and benzoate;

(h) combining the cell suspension and the modified basal medium to form a modified basal medium cell suspension;

(i) incubating the modified basal medium cell suspension until a CHC concentration of at least 7.8 mM has been achieved therein; and (j) purifying the CHC to provide substantially purified CHC.

14. The method of claim 13, wherein the crotonate salt is sodium crotonate.

15. The method of claim 13, wherein the crotonate salt is potassium crotonate.

16. The method of claim 13, wherein the growth medium of step (a) comprises the crotonate salt at a concentration in a range of about 30 mM to about 120 mM.

17. The method of claim 13, wherein the anoxic potassium phosphate buffer of step (d) has a concentration of about 50 mM and a pH of about 7.0, and was reduced with cysteine-sulfide solution.

18. The method of claim 17, wherein the cysteine-sulfide solution is a 2.5% solution.

19. The method of claim 13, wherein the first basal medium and the modified basal medium are anoxic.

20. The method of claim 13, wherein the modified basal medium of step (g) comprises crotonate salt at a concentration of at least 30 mM and benzoate at a concentration of at least 5 mM.

21. The method of claim 13, wherein the growth medium of step (a) comprises a yeast extract in a concentration in a range of about 5 g/l to about 15 g/l.

22. The method of claim 13, wherein the modified basal medium of step (g) comprises crotonate salt in a concentration of from about 30 g/l to about 120 g/l.

23. The method of claim 13, wherein the modified basal medium of step (g) comprises benzoate in a concentration of about 7.5 g/l to about 20 g/l.

24. The method of claim 13, wherein the modified basal medium of step (g) comprises formate in a concentration of about 5 mM to about 15 mM.

* * * * *